US005763412A

United States Patent [19]

Khan et al.

[11] Patent Number: 5,763,412
[45] Date of Patent: Jun. 9, 1998

[54] FILM-FORMING COMPOSITION CONTAINING CHLORHEXIDINE GLUCONATE

[75] Inventors: Mohammad A. Khan, Sandy; Minh Q. Hoang, Taylorsville, both of Utah

[73] Assignee: Becton Dickinson and Company, Franklin Lakes, N.J.

[21] Appl. No.: 823,948

[22] Filed: Apr. 8, 1997

[51] Int. Cl.⁶ .............................. A61K 31/70; A61F 5/00
[52] U.S. Cl. .................................................. 514/23; 602/49
[58] Field of Search ........................... 424/78.03, 78.02, 424/78.06, 78.07; 602/49; 514/23

[56] References Cited

U.S. PATENT DOCUMENTS

| | | | |
|---|---|---|---|
| Re. 32,300 | 12/1986 | Gorman et al. | 514/635 |
| 2,804,073 | 8/1957 | Gallienne et al. | 128/156 |
| 3,855,140 | 12/1974 | Billany et al. | 252/106 |
| 3,960,745 | 6/1976 | Billany et al. | 252/106 |
| 4,199,567 | 4/1980 | Rankin | 424/173 |
| 4,374,126 | 2/1983 | Cardarelli et al. | 424/81 |
| 4,434,181 | 2/1984 | Marks, Sr. et al. | 424/326 |
| 4,456,543 | 6/1984 | Owens | 252/106 |
| 4,466,431 | 8/1984 | Tharrat et al. | 128/156 |
| 4,542,012 | 9/1985 | Dell | 428/28 |
| 4,584,192 | 4/1986 | Dell et al. | 424/81 |
| 4,587,266 | 5/1986 | Verdicchio | 514/635 |
| 4,900,721 | 2/1990 | Bansemir et al. | 514/25 |
| 4,919,837 | 4/1990 | Gluck | 252/106 |
| 4,981,678 | 1/1991 | Tomlinson | 424/45 |
| 5,164,107 | 11/1992 | Khan et al. | 252/106 |
| 5,173,291 | 12/1992 | Brink et al. | 424/78.06 |
| 5,308,611 | 5/1994 | Thompson | 428/78.07 |
| 5,334,388 | 8/1994 | Hoang et al. | 424/402 |
| 5,547,662 | 8/1996 | Khan et al. | 424/78.03 |

OTHER PUBLICATIONS

"Pluronic Polyols . . . Toxicity and Irritation Data," BASF Wyandotte Corporation, Industrial Chemical Group, Wyandotte, MI 48192, pp. 1–7.

"Technical Data On . . . Pluronic® Polyols," BASF Wyandotte Corporation, Organic Specialties & Fine Chemicals Dept., Parsippany, NJ 07054, pp. 1–11.

Primary Examiner—Gary L. Kunz
Attorney, Agent, or Firm—Eric M. Lee

[57] ABSTRACT

An antimicrobial film forming surgical site preparation composition includes a film forming material and an antimicrobial agent soluble in a fugitive solvent. The composition when applied to the skin surface forms a substantially water insoluble, substantially tack-free flexible film adherent to the skin surface. The film is capable of releasably retaining the antimicrobial agent to substantially inhibit microbial growth on the skin surface. The film releases sufficient antimicrobial agent to substantially eliminate the microorganisms normally present on the skin surface to prepare the surface for the procedure and continues to release the antimicrobial agent during the procedure and subsequent wound healing. The composition can be easily washed from fabric and does not stain the fabric even where the fabric is treated with chlorine bleach. In addition, a smooth continuous film is formed without the use of a separate plasticizer.

12 Claims, No Drawings

FILM-FORMING COMPOSITION CONTAINING CHLORHEXIDINE GLUCONATE

FIELD OF INVENTION

This invention relates to a surgical site preparation composition. More specifically, this invention relates to a film forming surgical site preparation composition having an antimicrobial agent that is released onto the skin. Even more specifically, this invention relates to an antimicrobial film forming surgical site preparation composition that has improved film forming properties and that can be easily washed from hospital bedding.

BACKGROUND OF THE INVENTION

The normal surface of the skin has a multiplicity of microorganisms on it. As long as the skin surface is intact, the microorganisms generally present no problem to the body, achieving some natural balance with each other. When a surgical procedure is conducted which breaches the natural barrier formed by the skin, it is important that these normally present microorganisms be prevented from entering the wound.

Various protocols to reduce or eliminate skin microorganisms have been developed and are generally practiced rigorously. The protocols generally involve a thorough scrubbing of the skin surface for a prescribed time with an antimicrobial agent such as isopropyl alcohol, an iodophor or polyvinylpyrrolidone iodine. If hair is present in the area, that area may possibly be shaved. The patient is then draped with sterile drapes so that only the immediate area of the procedure is exposed. Following the procedure, the wound area is covered with a dressing for isolation until healing is substantially complete.

These procedures are generally successful, with the occurrence of post-surgical infections being maintained at a low level in most situations. The goal of all these practices is to rapidly decrease the microbial count present on the skin, then prevent regrowth of the organisms during the period when the surgical site is open and during the subsequent healing process. However, during the procedure, the freshly scrubbed site may be subjected to blood, various body fluids and saline washes coupled with mechanical abrasion by sponges and the like. The effect of these washes may be to remove any residual antimicrobial agent and allow a regrowth of microorganisms that potentially may enter the open wound. Attempts have been made to address this problem by incorporating the antimicrobial agent into a film that is applied to the area on the skin where the surgical procedure will take place.

U.S. Pat. No. 4,374,126 to Cardelli et al. teaches a composition and method for forming a film from an alcohol soluble carboxylated polyacrylate which includes an antimicrobial agent, an adhesion promoter and a difunctional amide for crosslinking the polymer as the alcohol solvent evaporates. The film formed is thus resistant to body fluids, can remain on the skin for up to two days providing both initial and sustained anti-microbial activity.

U.S. Pat. No. 4,542,012 to Dell teaches a film forming polymer containing complexed iodine as a broad spectrum antimicrobial agent. The composition is applied to the skin from a volatile solvent, which when evaporated, leaves the iodine containing polymer film. The iodine is released from the film to provide antimicrobial action.

U.S. Pat. No. 5,173,291 to Brink teaches an iodine containing aqueous polymer emulsion which forms a film when applied to the skin surface. The film releases the iodine as an antimicrobial agent.

It is important in these film forming compositions that a smooth continuous film be formed so that the area on the skin where the surgical procedure is to take place remains covered by the film. Typically a plasticizer is used to provide toughness, ductility and flexibility to the film and ensure that a smooth film results.

Unfortunately, the above described compositions that use iodine as the microbial agent are not entirely satisfactory. This is because there is a desire in the medical community to avoid the use of iodine as an antimicrobial agent since iodine is corrosive to some materials used in the health care setting. In addition, under some conditions iodine can be an irritant. Alcohol also is problematic because its effectiveness as an antimicrobial is limited, it has no persistent effect as a germicide, it is an irritant and it is flammable. Thus there has been a move in the medical community toward the use of chlorhexidine as an antimicrobial agent.

One antimicrobial film forming surgical site preparation composition that addresses this problem is described in U.S. Pat. No. 5,547,662 to Khan et al. The composition disclosed there uses chlorhexidine diacetate as the antimicrobial agent and provides a visual indication of the area to which the composition has been applied by the use of a dye. The use of a dye is important because if alcohol or chlorhexidine is used as the antimicrobial agent, visualization of the area to which the film has been applied is difficult. Alcohol and chlorhexidine are water white and thus are difficult to see. Iodine does not have this problem because it is brown.

Although the antimicrobial film forming surgical site preparation composition disclosed in Khan et al. works for its intended purpose it could be improved. For example, it is known that chlorhexidine will stain fabric when the fabric is washed using chlorine bleach. Chlorine bleach is typically used in the hospital and other health care facilities to clean and disinfect bedding and patient gowns as well as other fabric material used in health care facilities.

In addition, with all of the above described antimicrobial film forming surgical site preparation compositions, it is important that an appropriate moisture transmission rate exist for the film once it is applied to the skin. If the moisture transmission rate is too low, any moisture generated between the patient's skin and the film cannot permeate through the film. If moisture is allowed to collect on the skin, the moisture provides a potential breeding ground for antimicrobial growth and can facilitate the delamination of the formed film.

SUMMARY OF THE INVENTION

It is therefore an object of this invention to provide an antimicrobial film forming surgical site preparation composition that provides a smooth, flexible, ductile and tough film.

It is another object of this invention to provide an antimicrobial film forming surgical site preparation composition that avoids the use of iodine as the antimicrobial agent.

It is yet another object of this invention to provide an antimicrobial film forming surgical site preparation composition that can be easily washed out of fabric and that allows the fabric to be disinfected with chlorine bleach without the antimicrobial film forming surgical site preparation composition staining fabric.

It is still another object of this invention to provide an antimicrobial film forming surgical site preparation composition that has a satisfactory moisture transmission rate.

The antimicrobial film forming surgical site preparation composition of this invention includes a fugitive solvent, a film forming material which is soluble in the fugitive solvent, and an antimicrobial agent which is soluble in the solvent and which is capable of being releasably retained in the film forming material. The film forming material and the antimicrobial agent are dissolved in the fugitive solvent for application to the surface area of the skin intended as a surgical site. As the fugitive solvent evaporates, the film forming material forms a substantially water insoluble, substantially tack-free flexible film which is adherent to the skin surface. The film is capable of releasing the antimicrobial agent and substantially inhibiting microbial growth on the skin surface during the surgical procedure and subsequent wound healing.

The fugitive solvent is a liquid that has appreciable volatility in the range of 25° C. to 40° C. such as isopropanol, ethanol, ethylene dichloride, acetone, ethyl acetate, 1,1,2-trichloro-trifluoroethane and the like which is capable of dissolving the components of the composition. Preferably, the fugitive solvent is ethyl alcohol.

The film forming material is an organic polymeric material such as ethyl cellulose, methoxy cellulose, hydroxypropyl cellulose, hydroxyethyl cellulose, hydroxypropylemethyl cellulose, polyvinylpyrrolidone/vinyl acetate copolymer and crosslinked pyrrolidone. Preferably the film forming material is ethyl cellulose.

The antimicrobial agent is present in a quantity sufficient to inhibit microbial growth on the surface of the skin. The antimicrobial agent is chlorhexidine gluconate.

Other elements may be included in the composition. For example, a non-ionic surfactant may be used to help release the antimicrobial agent from the film and to help produce a uniform film. A dye may be used to provide a visual indication of the exact area where the composition has been applied to the skin. And a fragrance may be used.

DETAILED DESCRIPTION OF THE INVENTION

The antimicrobial film forming surgical site preparation composition of this invention includes a fugitive solvent, a water insoluble film forming material soluble in the solvent and an antimicrobial agent soluble in the solvent. The antimicrobial agent is also releasably retained in the film forming material. The film forming material and the antimicrobial agent are applied to the skin surface with the fugitive solvent to form a substantially water insoluble, substantially tack-free flexible film after the solvent evaporates. The film is adherent to the skin surface and releases the antimicrobial agent onto the skin surface. This substantially eliminates microbial growth on the skin surface during the procedure and during wound healing.

The term "fugitive solvent" as used herein describes a solvent having an appreciable vapor pressure, hence it is volatile, at temperatures between about 25° C. and about 40° C. Suitable fugitive solvents are alcohols, esters, chlorinated hydrocarbons, esters and chlorofluorocarbons. Exemplary fugitive solvents include isopropanol, ethanol, ethyl acetate, trichloromethane, acetone and 1,1,2-trichlorotrifluorethane.

It has been found that where chlorhexidine gluconate is used as the antimicrobial agent, a number of surprising benefits are achieved. Chlorhexidine gluconate has an affinity for cellulosic material and acts as a plasticizer. Thus, where chlorhexidine gluconate is used with a cellulosic material, a smooth continuous film is formed. This effect is seen at chlorhexidine gluconate concentrations ranging from as low as about 0.05% to as high as about 3%. In addition, where chlorhexidine gluconate is used, no separate plasticizer is needed to form an acceptable film. Finally, the antimicrobial effect of the chlorhexidine gluconate is seen in concentrations as low as about 0.1%. Preferably, a concentration of about 0.8% to about 2% is used.

Consistent with the foregoing, suitable film forming materials include but are not limited to ethyl cellulose, methoxycellulose, hydroxyethyl cellulose, polyvinylpyrrolidone/vinyl acetate copolymer and crosslinked pyrrolidone. Preferably ethyl cellulose is used in a concentration of between about 3 percent to about 4 percent.

Since the chlorhexidine gluconate has an affinity for the film forming material, it binds with that material. Thus, if the film forming composition of this invention is spilled on fabric, the chlorhexidine gluconate is not absorbed by the fabric but instead stays with the film forming material. This facilitates the washing of the fabric. Thus even where chlorine bleach is used during the wash, insufficient amounts of the chlorhexidine gluconate remain on the fabric to allow it to stain. In addition, since no separate plasticizer, which typically would be sparingly water soluble, is used there is no other material that would be available to retain the chlorhexidine gluconate and the ethyl cellulose on the fabric to allow staining to occur. As shown below, even at chlorhexidine gluconate concentrations of about 3%, the use of the present invention results in no staining.

The antimicrobial film forming surgical site preparation composition of this invention may also include a non-ionic surfactant, a dye and a fragrance. Preferably a polyoxyethylene-polyoxypropylene condensate, i.e. a non-ionic surfactant, is used in a concentration of between about 2% and about 2.5%. Such a surfactant is a Pluronic® polyol sold by BASF Wyandotte Corporation of Wyandotte, Mich. Preferably a Pluronic L101 and a Pluronic L31 are used. In addition, preferably a yellow dye and a green dye are used in a total concentration of between about 0.09% and about 0.12%. Finally, preferably a Neutrogena fragrance is used in a concentration of between about 0.08% and about 0.12%.

The following examples are provided to illustrate the invention, but are not to be considered to be limitative of the invention.

EXAMPLE I

The laundrability of the antimicrobial film forming surgical site preparation composition of this invention was shown by pouring a small volume of the composition containing 1% chlorhexidine gluconate on a piece of fabric. The fabric was then dried and washed with a chlorine bleach and detergent solution. The washed fabric showed no signs of a stain from the composition. Separately, a piece of fabric was similarly treated with a 1% chlorhexidine gluconate solution in ethanol. The fabric was washed with a chlorine bleach and detergent solution. The washed fabric exhibited a brownish stain.

EXAMPLE II

The following compositions were made to assess the film integrity, antimicrobial effectiveness and staining properties of the antimicrobial film forming surgical site preparation composition of this invention.

| Ingredients | Comp. 1 | Comp. 2 | Comp. 3 | Comp. 4 | Comp. 5 | Comp. 6 | Comp. 7 | Comp. 8 |
|---|---|---|---|---|---|---|---|---|
| Denatured Ethyl Alcohol SD40 | 64.0 | 71.1 | 83.8 | 83.8 | 83.8 | 83.8 | 83.8 | 83.8 |
| Ethyl Cellulose | 3.5 | 3.9 | 3.5 | 3.5 | 3.5 | 3.5 | 3.5 | 3.5 |
| Chlorhexidine Gluconate | 5.0 | 3.3 | 0.3 | 0.1 | 0.05 | 0.01 | 0.005 | 0.001 |
| Pluronic L101 | 2.0 | 2.2 | 2.0 | 2.0 | 2.0 | 2.0 | 2.0 | 2.0 |
| Pluronic L31 | 0.3 | 0.33 | 0.3 | 0.3 | 0.3 | 0.3 | 0.3 | 0.3 |
| D&C Yellow No. 10 | 0.1 | 0.11 | 0.1 | 0.1 | 0.1 | 0.1 | 0.1 | 0.1 |
| FD&C Green No. 3 | 0.005 | 0.006 | 0.005 | 0.005 | 0.005 | 0.005 | 0.005 | 0.005 |
| Purified Water | 24.5 | 18.35 | 9.4 | 9.6 | 9.7 | 10.0 | 9.9 | 9.74 |
| Neutrogena Fragrance | 0.1 | 0.11 | 0.1 | 0.1 | 0.1 | 0.1 | 0.1 | 0.1 |

Film Integrity

The films formed from these various compositions were examined for their smoothness, flakiness and cracking. Although the film cast with Composition No. 1 was slightly sticky, cruddy, and cloudy it was acceptable. The films formed from compositions 2, 3 and 4 were uniform with no cracks or flakes. Film cast with example Composition No. 5 was acceptable. However, the quality of the film was not as good because it showed cracks in the film. Similarly, the quality of the film cast with Composition Nos. 6, 7 and 8 deteriorated as the concentration of chlorhexidine was reduced from 0.01% to 0.001%.

Laundry Staining

Composition Nos. 1 and 2 were used to check the staining properties of the antimicrobial film forming surgical site preparation composition of this invention. When a small volume of Composition No. 1 was applied to fabric and the fabric was washed in a chlorine bleach and detergent solution, the fabric was stained. However, when a small volume of Composition No. 2 was tried, no staining occurred.

Antimicrobial Effectiveness

Composition Nos. 3, 4, 5 and 6 were tested for zone of inhibition. The results are described below.

| Comp. No. | mm Zone of Inhibition; S. Aureaus | mm Zone of Inhibition; P. Aeruginosa |
|---|---|---|
| 3 | 15 | Vague zone with no growth under the film |
| 4 | 9 | Vague zone with no growth under the film |
| 5 | Vague Zone | Positive growth under the film |
| 6 | No Zone | Positive growth under the film |

EXAMPLE III

Since chlorhexidine gluconate has an affinity for cellulosic material, it binds with ethyl cellulose and holds the molecules together. When a film is cast out of the composition of the present invention, the film is held together and appears smooth without any flakiness or cracks. If the chlorhexidine gluconate is not present in the solution, the film produced out of the solution is not uniform. The film shows white flakes and the film cracks. This observation was confirmed by conducting the following experiment.

| Ingredients | Comp. No. 1 | Comp. No. 2 | Comp. No. 3 | Comp. No. 4 | Comp. No. 5 |
|---|---|---|---|---|---|
| Denatured Ethyl Alcohol SD40 | 83.8 | 83.8 | 83.8 | 83.8 | 83.8 |
| Ethyl Cellulose | 3.5 | 3.5 | 3.5 | 3.5 | 3.5 |
| Chlorhexidine gluconate | 1.04 | — | — | — | — |
| Pluronic L101 | 2.0 | 2.0 | 2.0 | 2.0 | 2.0 |
| Pluronic L31 | 0.3 | 0.3 | 0.3 | 0.3 | 0.3 |
| D&C Yellow No. 10 | 0.1 | 0.1 | 0.1 | 0.1 | 0.1 |
| FD&C Yellow No. 3 | 0.005 | 0.005 | 0.005 | 0.005 | 0.005 |
| Purified Water | 9.16 | 10.2 | 9.16 | 9.2 | 9.2 |
| Neutrogena Fragrance | 0.1 | 0.1 | 0.1 | 0.1 | 0.1 |
| Para-chloro-meta-xylenol | — | — | — | 1.0 | — |
| Polyhexamethylene biguanidine hydrochloride | — | — | 1.04 | — | — |
| Iodine | — | — | — | — | 1.0 |

Film Casting

Twenty-five grams of each of the compositions was poured into a 98 mm diameter plastic petri dish. The dish was then placed under the hood at room temperature for the solvent to evaporate overnight. The film thus produced was examined. The results are described below.

| Film From Composition No. | Film Characteristics |
|---|---|
| 1 | Nice uniform film, no cracks or flakes |
| 2 | Discontinuous, cracked, and flaky film |
| 3 | Discontinuous, cracked and flaky film |
| 4 | Discontinuous, cracked and flaky film |
| 5 | Film hard to dry, dried area cracked and flaky |

The above result clearly indicate that chlorhexidine gluconate uniquely acts as a binder for the film and produces a uniform film.

EXAMPLE IV

The following experiment shows the surprising benefits of the composition of the present invention are achieved only by using chlorhexidine gluconate in combination with ethyl cellulose.

| Ingredients | Composition No. 1 (w/w) | Composition No. 2 (w/w) |
|---|---|---|
| Ethyl cellulose | 3.5 | 3.5 |
| Propylene glycol methyl ether PM | 15.0 | — |
| Isopropyl alcohol | 73.0 | — |

| Ingredients | Composition No. 1 (w/w) | Composition No. 2 (w/w) |
| --- | --- | --- |
| Pluronic L 101 | 2.0 | 2.0 |
| Pluronic L31 | 0.3 | 0.3 |
| Chlorhexidine diacetate | 1.0 | 1.0 |
| Water | 5.0. | 9.2 |
| D&C Yellow No. 10 | 0.1 | 0.1 |
| FD&C Green No. 3 | 0.005 | 0.005 |
| Neutrogena Fragrance | 0.1 | 0.1 |
| Ethanol SD40 | — | 83.8 |

Results

Composition No.1 provides a very uniform film when 25 g of the composition is poured into the petri dish and the solvent is allowed to evaporate. In the laundry stain test, this composition produces a light brownish stain on the cloth as a result of the reaction with chlorine bleach in the wash. Composition No. 2 fails to produce an acceptable film. The film was very flaky, not uniform, and had cracks all over. In the laundry stain test, this composition did not produce the characteristic brown stain in the wash which contained detergent and chlorine bleach.

EXAMPLE V

The moisture transmission rate of the film formed from the composition of the present invention was determined by the following experiment. Approximately 2.5" diameter pieces of Tyvek® 1059B sheets were generously painted on the rough side with the composition of the present invention to simulate the application on the skin. After drying, a smooth and uniform film was formed. Sheets without the film were used as controls. The water-vapor transmission rate was determined by using the Fisher/Payne permeability cup. The results are tabulated below. For comparison, water-vapor transmission rates of several commercially available I.V. transparent dressing are also reported.

| Product | Moisture Transmission Rate ($gH_2O/M^2/day$) |
| --- | --- |
| 1. Tyvek ® 1059B | 1265 |
| 2. Tyvek ® 1059B with Film formed from composition of the invention | 1081 |
| 3. Opsite ® Transparent Catheter Dressing | 626 |
| 4. Tegaderm ® Transparent Catheter Dressing | 502 |
| 5. Bioclusive Transparent Dressing | 486 |

These results indicate that when the composition of the present invention is applied to Tyvek® 1059B sheets, the resulting film is permeable to moisture and in fact, has a higher moisture transmission rate than several commercially available dressings.

EXAMPLE VI

Another experiment was conducted using different film forming materials.

| Ingredients | Comp. 1 | Comp. 2 | Comp. 3 | Comp. 4 | Comp. 5 |
| --- | --- | --- | --- | --- | --- |
| Ethyl SD40 | 70.0 | 68.0 | 70.0 | 68.0 | 83.8 |
| Hydroxypropyl methyl cellulose | 1.5 | 1.5 | — | — | — |
| Hydroxypropyl cellulose | — | — | 1.5 | 1.5 | — |
| Polyvinylpropyrrolidone | — | — | — | — | 3.51 |
| K90 | | | | | |
| Pluronic L101 | 2.0 | 1.9 | 2.0 | 1.9 | 2.0 |
| Pluronic L31 | 0.3 | 0.3 | 0.3 | 0.3 | 0.3 |
| Chlorhexidine gluconate | 0.3 | 0.98 | 0.3 | 0.98 | 1.04 |
| D&C Yellow No. 10 | 0.1 | 0.1 | 0.1 | 0.1 | 0.1 |
| FD&C Green No. 3 | 0.005 | 0.005 | 0.005 | 0.005 | 0.005 |
| Water | 25.2 | 26.92 | 25.2 | 26.92 | 8.66 |
| Neutrogena Fragrance | 0.1 | 0.1 | 0.1 | 0.1 | 0.1 |

Film Quality

The films produced from Composition Nos. 1, 2, 3 and 4 were sticky and took a long time to dry. This is due to the fact that both hydroxypropyl cellulose and hydroxypropyl methyl cellulose are water soluble. The film produced from Composition No. 5 dried much faster compared to the films formed from Composition Nos. 1, 2, 3 and 4. However, the film formed from Composition No. 5 was sticky. Again, this is due to the fact that polyvinyl pyrrolidone is soluble in water and is sticky in nature when it is in contact with moisture. The film quality was good in all the examples. No cracks or flakiness were observed. When applied on the skin, all of the above compositions form a non-sticky film.

Laundry Staining

All of the compositions did not produce the characteristic stain of chlorhexidine when fabric containing a small volume of the composition was washed in detergent containing chlorine bleach.

Test Procedure For Zone Of Inhibition

Mueller Hinton agar plates are inoculated with standardized broth culture (titer=approximately $10^8$ count per ml) by evenly streaking in two directions over the entire surface of the plate with a saturated cotton swab. After the inoculum is dried, a 6 mm sample disk is embedded into the agar. The plates are inverted and incubated at 37° C. overnight. The clearing zones of inhibition are measured and reported as diameter (mm) clearing zone from one edge to the other. The clearing zones include the 6 mm diameter disk size.

| | Zone of Inhibition | |
| --- | --- | --- |
| Comp. No. | MM Zone of Inhibition S. aureus | MM Zone of Inhibition P. aeruginosa |
| 1 | 19 | 10 |
| 2 | 22 | 13 |
| 3 | 20 | 11 |
| 4 | 20 | 12 |
| 5 | 25 | 13 |

The test results indicate that all of the films from these compositions are very effective against S. aureus and P. aeruginosa.

EXAMPLE VII

The following compositions were made to demonstrate the difference between films containing either chlorhexidine gluconate or chlorhexidine diacetate without any surfactants.

| Ingredients | Comp. No. 1 (W/W) | Comp. No. 2 (W/W) |
| --- | --- | --- |
| Ethanol SD40 | 83.8 | 83.8 |
| Ethyl cellulose | 3.5 | 3.5 |

-continued

| Ingredients | Comp. No. 1 (W/W) | Comp. No. 2 (W/W) |
|---|---|---|
| Chlorhexidine gluconate | 1.0 | — |
| Chlorhexidine diacetate | — | 1.0 |
| Water | 11.7 | 11.7 |

Ethyl cellulose was first dissolved into ethanol and the rest of the ingredients were mixed. Films were cast by pouring 25 g of the solution into a petri dish and evaporating the solvent overnight.

Test Results

| Film Quality: | The film formed from Composition No. 1 was continuous with no flakiness and no cracks. The film formed from Composition No. 2 showed flakiness and cracks. |
|---|---|
| Laundry Staining: | The film formed from Composition No. 1 did not stain the fabric when treated with detergent and chlorine bleach. The film formed from Composition No. 2 produced the characteristic brown stain when the fabric was treated with detergent and chlorine bleach. The two films were tested for zone of inhibition according to the procedure reported earlier. The results are given below. |

Zone of Inhibition:

| | (mm) Diameter Clearing Zone S. Aureus | (mm) Diameter Clearing Zone E. Coli |
|---|---|---|
| Composition No. 1 | 22 | 20 |
| Composition No. 2 | 13 | 16 |

Thus it is seen that an antimicrobial film forming surgical site preparation composition is provided that provides a tough, ductile, flexible and smooth film, that avoids the use of iodine as the antimicrobial agent and that easily washes out of fabric without staining, even in the presence of chlorine bleach and that provides a satisfactory moisture transmission rate.

What is claimed is:

1. An antimicrobial film forming surgical site preparation composition, comprising:

a fugitive solvent;

a film forming material soluble in the solvent; and chlorhexidine gluconate at a weight to weight concentration of about 0.05% to about 3%.

2. The composition of claim 1 wherein said fugitive solvent is selected from the group consisting of isopropanol, ethanol, ethylene dichloride, acetone, ethyl acetate and 1,1, 2-trichloro-trifluoroethane.

3. The composition of claim 2 wherein said film forming material is selected from the group consisting of ethyl cellulose, methoxy cellulose, hydroxypropyl cellulose, hydroxyethyl cellulose, hydroxypropylmethyl cellulose, polyvinyl pyrrolidone, vinyl acetate, and cross linked pyrrolidone.

4. An antimicrobial film forming surgical site preparation composition comprising a homogeneous solution of:

5. The composition of claim 4 further comprising a non-ionic surfactant.

6. The composition of claim 5 wherein the non-ionic surfactant is a polyoxyethylene-polyoxypropylene condensate.

7. The composition of claim 6 wherein the polyoxyethylene-polyoxypropylene condensate comprises between about 2% and about 2.5% of the composition.

8. An antimicrobial film forming surgical site preparation composition, comprising:

a fugitive solvent;

a film forming material soluble in the solvent; and chlorhexidine gluconate where the composition does not contain a separate plasticizer to form an acceptable film.

9. The composition of claim 8 wherein the chlorhexidine gluconate is present in a quantity ranging between about 0.05% to about 3%.

10. The composition of claim 9 wherein the film forming material is ethyl cellulose.

11. The composition of claim 9 wherein the ethyl cellulose is present in a quantity ranging from about 3% to about 4%.

12. The composition of claim 11 wherein the fugitive solvent is ethyl alcohol.

* * * * *